(12) United States Patent
Ozcan et al.

(10) Patent No.: US 11,284,914 B2
(45) Date of Patent: Mar. 29, 2022

(54) VESSEL SEALING AND CUTTING SYSTEM BY MEANS OF EXTRA-LUMINAL LASER

(71) Applicant: Istanbul Universitesi Rektorlugu, Istanbul (TR)

(72) Inventors: Murat Ozcan, Istanbul (TR); Mustafa Tunaya Kalkan, Istanbul (TR); Ozan Onur Balkanay, Istanbul (TR); Akif Enes Arikan, Istanbul (TR)

(73) Assignee: Istanbul Universitesi Rektorlugu, Istanbul (TR)

( * ) Notice: Subject to any disclaimer, the term of this patent is extended or adjusted under 35 U.S.C. 154(b) by 481 days.

(21) Appl. No.: 16/465,363

(22) PCT Filed: Jul. 4, 2017

(86) PCT No.: PCT/TR2017/050304
§ 371 (c)(1),
(2) Date: May 30, 2019

(87) PCT Pub. No.: WO2018/101897
PCT Pub. Date: Jun. 7, 2018

(65) Prior Publication Data
US 2019/0388114 A1 Dec. 26, 2019

(30) Foreign Application Priority Data

Nov. 30, 2016 (TR) ................................ 2016/17493

(51) Int. Cl.
*A61B 17/285* (2006.01)
*A61B 18/20* (2006.01)
(Continued)

(52) U.S. Cl.
CPC .......... *A61B 17/285* (2013.01); *A61B 18/20* (2013.01); *A61B 2017/00477* (2013.01);
(Continued)

(58) Field of Classification Search
CPC .............. A61B 17/285; A61B 17/2804; A61B 2017/2808; A61B 17/2812;
(Continued)

(56) References Cited

U.S. PATENT DOCUMENTS

| 5,147,356 A | 9/1992 | Bhatta |
| 5,507,742 A | 4/1996 | Long et al. |

(Continued)

FOREIGN PATENT DOCUMENTS

| TR | 201617493 | 11/2016 |
| WO | 2015121866 A1 | 8/2015 |
| WO | 2018101897 A1 | 6/2018 |

OTHER PUBLICATIONS

Foreign communication from a related counterpart application—International Search Report and Written Opinion, PCT/TR2017/050,304, filed Oct. 12, 2017, 9 pages.

*Primary Examiner* — Aaron F Roane
(74) *Attorney, Agent, or Firm* — Conley Rose, P.C.; Rodney B. Carroll

(57) ABSTRACT

The present invention is a vessel sealing and cutting system (10) comprising a surgical equipment (20) comprising a lower jaw (222) and an upper jaw (212) in a manner defining a holder tip (24) grabbing the tissues containing vessels, and a lower body (21) embodied at the continuation of said upper jaw (212), and a laser source (50) connected to said surgical equipment (20), characterized by comprising a module housing (215) embodied in a manner extending inside said lower body (21) and said upper jaw (212), and a laser module (30) which transmits a laser light to the grabbing region (61) from said holder tip (24) in a simultaneous manner with the closing of the jaws and positioned in said module housing (215) in a manner connected to said laser source (50) from one end thereof.

14 Claims, 5 Drawing Sheets

(51) Int. Cl.
  *A61B 17/00* (2006.01)
  *A61B 17/28* (2006.01)
  *A61B 18/00* (2006.01)
  *A61B 18/22* (2006.01)

(52) U.S. Cl.
  CPC .......... *A61B 2017/2825* (2013.01); *A61B 2018/0063* (2013.01); *A61B 2018/00428* (2013.01); *A61B 2018/00601* (2013.01); *A61B 2018/00922* (2013.01); *A61B 2018/2277* (2013.01)

(58) Field of Classification Search
  CPC .......... A61B 17/2816; A61B 17/282; A61B 2017/2825; A61B 2017/2829; A61B 17/2833; A61B 2017/2837; A61B 17/2841; A61B 2017/2845; A61B 18/20; A61B 2017/00477; A61B 2018/00428; A61B 18/00601; A61B 18/00589; A61B 18/00595; A61B 2018/0063; A61B 2018/00922; A61B 2018/2277
  USPC .......................................................... 606/13
  See application file for complete search history.

(56) References Cited

U.S. PATENT DOCUMENTS

| | | | |
|---|---|---|---|
| 7,951,150 B2 | 5/2011 | Johnson et al. | |
| 2013/0253489 A1* | 9/2013 | Nau, Jr | A61B 17/29 606/16 |
| 2014/0121508 A1* | 5/2014 | Latimer | A61B 18/20 600/427 |
| 2015/0238260 A1* | 8/2015 | Nau, Jr. | A61B 5/4041 606/15 |
| 2015/0359581 A1* | 12/2015 | Albertal | A61B 18/14 606/49 |

\* cited by examiner

VESSEL SEALING AND CUTTING SYSTEM BY MEANS OF EXTRA-LUMINAL LASER

CROSS REFERENCE TO RELATED APPLICATIONS

This application is a filing under 35 U.S.C. 371 of International Application No. PCT/TR2017/050304 filed Jul. 4, 2017, entitled "Vessel Sealing and Cutting System by Means of Extra-Luminal Laser" which claims priority to Turkish Patent Application No. 2016/17493 filed Nov. 30, 2016, which applications are incorporated by reference herein in their entirety.

TECHNICAL FIELD

The present invention relates to a system where vessel sealing and cutting processes are realized in an extra-luminal manner by means of laser during surgical operations and interventions.

KNOWN STATE OF THE ART

When required during surgical interventions, the vessels shall be closed in cases of undesired bleeding occurred in the surgical field. In ancient times, when this process is first tried, the vessel was held and cut with scalpel or surgical scissors and afterwards the ends of the vessel were cauterized. In cases where the diameter of the vessel was wide, since the cauterization process was insufficient, the two ends of the vessel were separately ligated. Together with the technological developments, this process was begun to be established by using electro-cautery. Electro-cauteries reach approximately 250° C. and they provide closing of the vessel by means of cauterization. Together with the technological developments, cauteries have been turned into energy based devices which utilize bipolar electrical power and afterwards, cauteries have been turned into devices which utilize ultrasonic power.

In the U.S. Pat. No. 7,951,150, an electrosurgical instrument includes a housing having a shaft attached thereto which defines a longitudinal axis there through. The instrument also includes first and second opposing jaw members coupled to the shaft, the first jaw member having a conductive surface and movable relative to the second jaw member. The second jaw member is fixed relative to the shaft and includes an electrode rotatable along the longitudinal axis. The rotatable electrode has a sealing surface and a cutting edge. The cutting structures provided in the jaw members are heated by means of power supply and cauterization process is realized together with the cutting process. The power supply is an electrical source. During the cauterization process, only the vessel, which is to be cut and cauterized, shall be heated. Otherwise, the other adjacent tissues are heated and damaged so lose their function transiently or permanently. In the cauteries which function with microwave, ultrasonic or resistance, this cannot be provided and undesired energy transfer occurs to the adjacent tissues existing in the application area and heating occurs. Another disadvantage which occurs in such cauteries, sealing of vessels with diameter of maximum 6-8 mm can be realized, and simultaneous cutting is not possible.

In the U.S. Pat. No. 5,507,742, an endoscopic tool has an elongate cylindrical cannula with an open hooked end insertable into the body of a patient with a trocar element providing a laser powered flux of energy for precise incision and optional cauterization of tissue. A conventional pointed trocar may be used with the hooked cannula to permit forcible insertion of the hooked cannula end to the selected surgical site. In the alternative, a laser energy conveying trocar may be used with the hooked cannula or homeostatic insertion into the patient's body. The basic disadvantage of said application is that it is insufficient for large vessels. The reason of this is that the whole cutting and cauterizing process is realized by means of laser. Thus, there is no force exerted for closing the vessel ends. Therefore, it is considered that, only the laser ray is not sufficient for closing the vessel end except very small vessel structures. Therefore, resistance to high pressure exposure decreases and there occurs the risk of bleeding in the region where cauterizing is planned to be realized and depending on this, there is increased risk of blood loss and complication proportions of the intervention, and prolongation of duration of the operation. Another disadvantage of this system is that the laser application manner has the risk of external ray radiation and damaging the adjacent tissues due to heat radiation.

In the U.S. Pat. No. 5,147,356, the invention provides a surgical instrument which provides cutting and cauterizing of exposed vessels. There is a cable which reaches one of the cutting ends of said instrument. The cable provides the required heat for the cutting end. In an alternative embodiment of the invention, it is mentioned that this cable can be fiber and can carry laser rays. However, in the specification, it is not mentioned how the operation is to be realized by using laser.

The common disadvantage of all of the abovementioned systems is that usage costs are high since these systems are disposable (single-use). Repetitive sterilization processes are realized for reducing the high usage costs, however, risky conditions occur in terms of patient safety in this case.

BRIEF DESCRIPTION OF THE INVENTION

The present invention relates to a vessel sealing and cutting system by means of laser in an extra-luminal manner (through the outer surface of the vessels), for eliminating the abovementioned disadvantages and for bringing new advantages to the related technical field.

The object of the present invention is to provide a vessel sealing and cutting system which functions by means of laser energy and which provides simultaneous sealing and cutting of vessels.

Another object of the present invention is to provide a vessel sealing and cutting system which provides joining of vessel walls to each other by means of controlled laser energy besides mechanical tightening.

Another object of the present invention is to provide a vessel sealing and cutting system which reduces the usage costs by means of a re-usable laser processing mechanism.

Another object of the present invention is to provide a vessel sealing and cutting system for increasing patient safety by means of usage of a disposable surgical equipment which has low cost.

Another object of the present invention is to provide a vessel sealing and cutting system which covers all of the open and endoscopic surgical interventions by means of usage of disposable surgical equipment and which supports the variations used in different methods.

Another object of the present invention is to provide a vessel sealing and cutting system whose usage safety has been increased.

In order to realize all of the abovementioned objects and the objects which are to be deducted from the detailed description below, the present invention is a vessel sealing and cutting system comprising a surgical equipment comprising a lower jaw and an upper jaw in a manner defining a holder tip grabbing the vessels in vessel containing tissues, and a lower body embodied at the continuation of said upper jaw, and a laser source connected to said surgical equipment. Accordingly, the subject matter invention is characterized by comprising a module housing embodied in a manner extending inside said lower body and said upper jaw, and a laser module which transmits a laser light to the grabbing region from said holder tip in a simultaneous manner with the closing of the jaws and positioned in said module housing in a manner connected to said laser source from one end thereof.

In a preferred embodiment of the invention, said laser module comprises an outer body placed into the lower body and a tip part is embodied at the continuation of the outer body placed into the upper jaw.

In another preferred embodiment of the invention, a triggering region, which is aligned with a trigger provided on the surgical equipment as the laser module is placed to the lower body, is embodied on the outer body.

In another preferred embodiment of the invention, a connection part is provided at one end of the outer body, and a connector housing is positioned at the end of said connection part and whereto said laser source is connected.

In another preferred embodiment of the invention, a tab opening is embodied at said connection part and a module connection pin is provided under the connection part.

In another preferred embodiment of the invention, at least one connection tab is provided at the lower body in a manner corresponding to said tab opening.

In another preferred embodiment of the invention, in order to provide completion of the circuit such that the system interacts with the laser source, a module connection housing, wherein said module connection pin is placed, is embodied at the lower body.

In another preferred embodiment of the invention, an optical opening is embodied at the upper jaw in a manner providing transmission of the light guided from the upper jaw to the grabbing region through the tip part.

In another preferred embodiment of the invention, a laser processing mechanism is provided in said outer body in a manner providing guidance of the light, generated by the laser source, through the optical opening.

In another preferred embodiment of the invention, said laser processing mechanism comprises an inner transmission line connected to the laser source, and a regulatory lens, a focusing lens and a prism positioned inside the outer body respectively and which transmit a light, exiting said inner transmission line, to the tip part.

In another preferred embodiment of the invention, the laser processing mechanism comprises an optical opening area embodied at the tip part which will provide guidance of the light, exiting the prism, to the optical opening.

In another preferred embodiment of the invention, a line opening embodied at the end of the inner transmission line and the inner transmission line comprises a primary fixation part and a secondary fixation part to provide fixation of the inner transmission line.

In another preferred embodiment of the invention, the light, transmitted from the line opening of the transmission line to the optical opening area, is a light beam.

In another preferred embodiment of the invention, the light beam, which exits the line opening and which is transmitted to the regulatory lens, is a main light beam.

In another preferred embodiment of the invention, the light beam, which exits the regulatory lens and which is transmitted to the focusing lens, is a linear light beam.

In another preferred embodiment of the invention, the light beam, which exits the focusing lens and which is transmitted to the prism, is a focused light beam.

In another preferred embodiment of the invention, the light beam, guided from the prism to the optical opening area, is a directed light beam.

In another preferred embodiment of the invention, a thermo-stable part is provided where said lower jaw and said upper jaw are covered in a manner increasing the tightening effect of the tissue.

REFERENCE NUMBERS

10 Vessel Sealing and Cutting System
20 Surgical Equipment
   21 Lower Body
      211 Handle
      212 Upper Jaw
      213 Optical Gap
      214 Connection Tab
      215 Module Housing
      216 Module Connection Housing
      217 Trigger
      218 Safety Lock
   22 Upper Body
      221 Grabber Handle
      222 Lower Jaw
   23 Hinge Point
   24 Holder Tip
   25 Thermo-stable Part
   26 Surface Coating
30 Laser Module
   31 Outer Body
      311 Tip Part
      312 Triggering Region
   32 Connection Part
      321 Module Connection Pin
      322 Tab Opening
      323 Connector Housing
40 Laser Processing Mechanism
   41 Inner Transmission Line
      411 Primary Fixation Part
      412 Secondary Fixation Part
      413 Line Opening
   42 Regulatory Lens
   43 Focusing Lens
   44 Prism 45 Optical Opening Area
46 Light Beam
   461 Main Light Beam
   462 Linear Light Beam
   463 Focused Light Beam
   464 Directed Light Beam
50 Laser Source
  51 Laser Tube
  52 Laser Generator
  53 Transmission Line
  54 Connector
60 Operation Region
  61 Grabbing Region
  62 Laser Axis
  63 Tissue

DETAILED DESCRIPTION OF THE INVENTION

In this detailed description, the subject matter of innovation is explained with references to examples only in order to make the subject more understandable without forming any restrictive effect. Accordingly, a vessel sealing and cutting system (10) is described which comprises a surgical equipment (20) used in surgical operations and which provides sealing of the vessel during transection and which functions by means of laser, and said vessel sealing and cutting system (10) further comprises structural components related to the surgical equipment.

Figure 1:
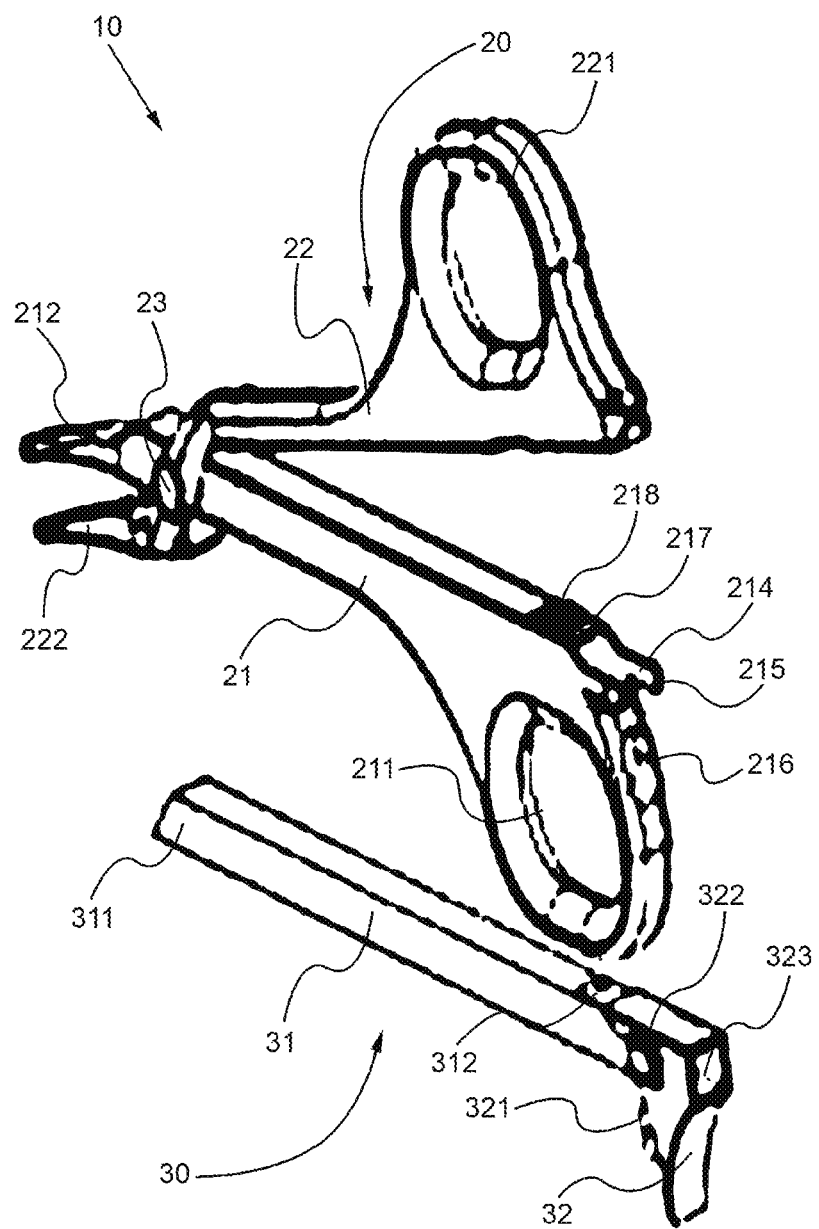
In FIG. 1, the general view of the vessel sealing and cutting system is given.

In FIG. 1, the general view of a system used for sealing and cutting of vessels is given. The sealing and cutting system (10) basically consists of surgical equipment (20) which holds the vessel containing tissue and a laser module (30) related to said surgical equipment (20). Said laser module (30) is connected to a laser source (50) in order to realize cutting and sealing process.

Figure 2:
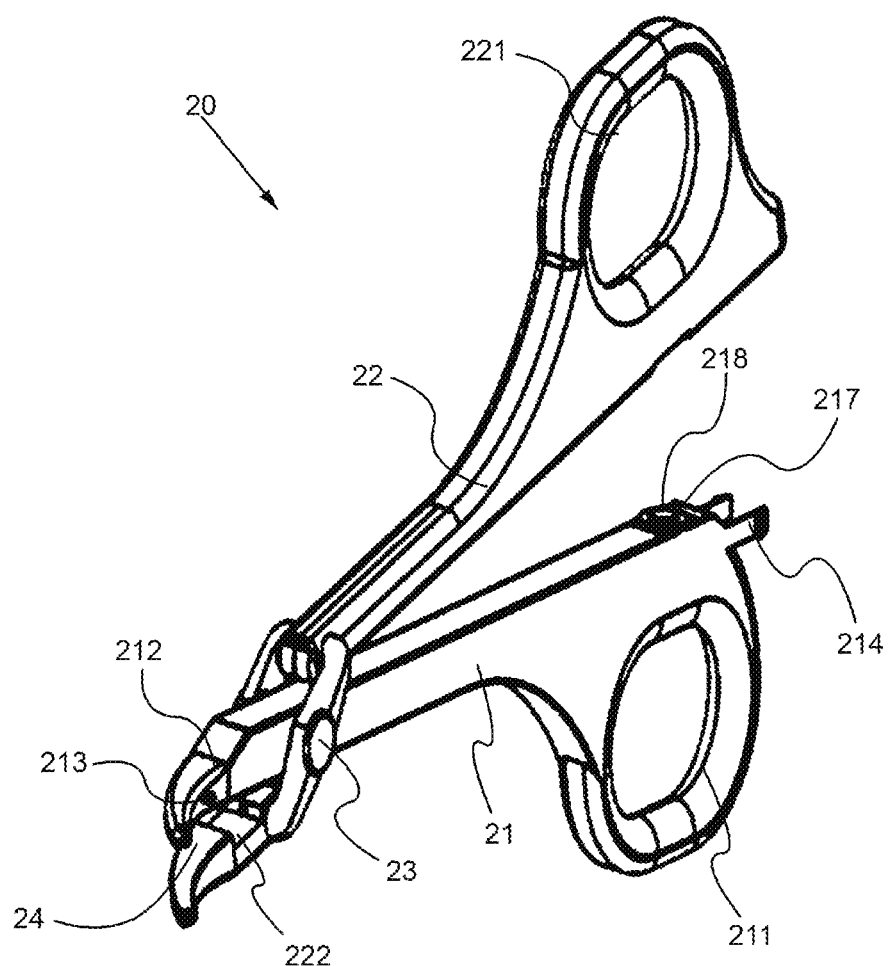
In FIG. 2, the general view of the surgical equipment related to the vessel sealing and cutting system is given.
Figure 3:
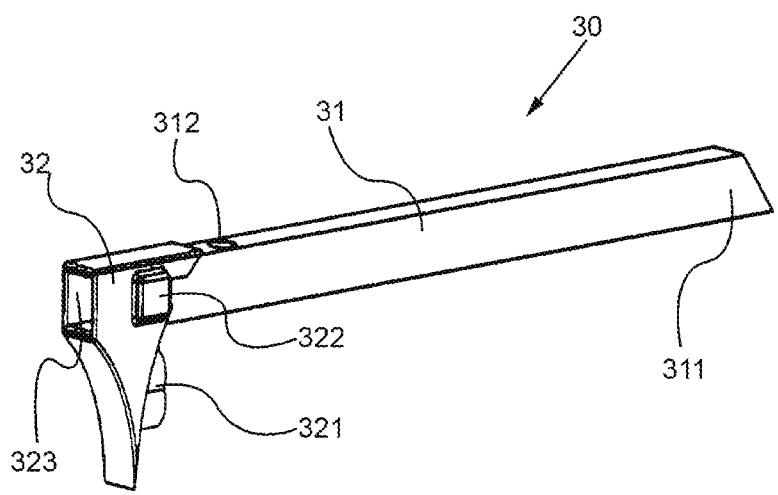
In FIG. 3, the general view of the laser module of the vessel sealing and cutting system is given.

The surgical equipment (20) whose general and detailed views are given in FIGS. 2 and 3 basically comprises a fixed lower body (21) and an upper body (22) connected to said lower body (21) through a hinge point (23) and which is movable around said hinge point (23). The lower body (21) comprises a handle (211) at one end and an upper jaw (212) at the other end. Said upper body (22) comprises a gripping handle (221) at one end and a lower jaw (222) at the other end. Said lower jaw (222) and said upper jaw (212) form the holder tip (24) together. There is a module housing (215) embodied in said lower body (21) in a manner extending inside the lower body (21). There is a trigger (217) on the lower body (21) and there is a safety lock (218) provided on said trigger (217). There are two connection tabs (214) provided side by side at the region where the lower body (21) and the handle (211) are jointed. A module connection housing (216) is embodied at the end of the handle (211). An optical opening (213) is embodied on the lateral surface of the upper jaw (212). The surfaces of both the upper jaw (212) and the lower jaw (222), which face each other, comprise a thermo-stable part (25). The upper side of said thermo-stable part (25) is covered by a surface coating (26).

Figure 4:
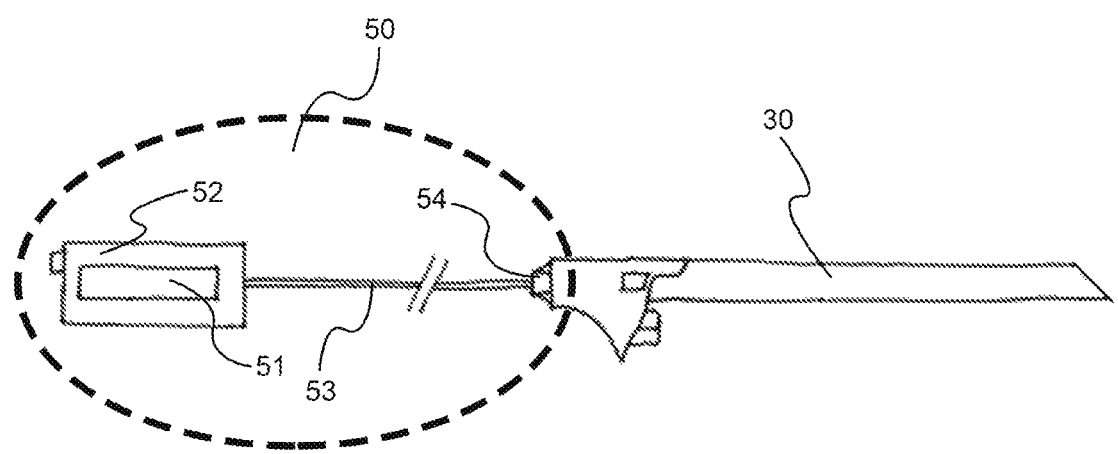
In FIG. 4, the schematic view of the laser module and the related laser source is given.
Figure 5:
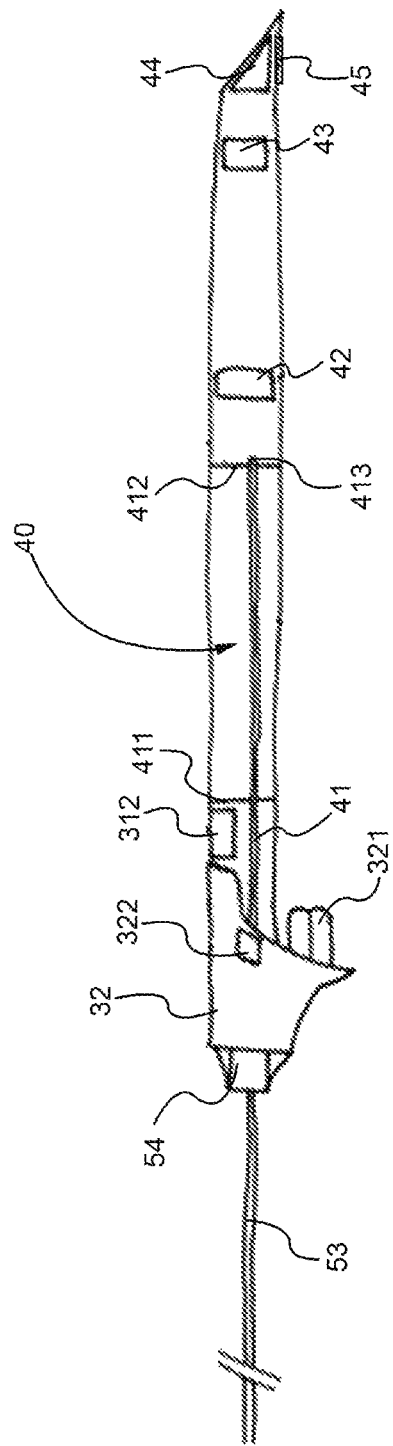
In FIG. 5, the detailed view of the laser module and the related laser processing mechanism is given.

In FIGS. 4 and 5, the laser module (30) and the laser source (50) connected to the laser module (30) are illustrated. In accordance with these figures, the laser module (30) consists of an outer body (31) and a connection part (32) connected at the end of said outer body (31). A tip part (311) is embodied at the continuation of the outer body (31). There is a triggering region (312) embodied in the region where said connection part (32) ends on the outer body (30). A connection housing (323) is embodied at the end of the connection part (32), and a tab opening (322) is embodied on the connection part (32). A module connection pin (321) extends under the connection part (32). Said laser source (50) is connected to the laser module (30) through said connector housing (323). The laser source (50) comprises a laser tube (51), a laser generator (52) connected to said laser tube (51), a transmission line (53) exiting said laser generator (52), and a connector (54) provided at the continuation of said transmission line (53). The connection between said laser module (30) and said laser source (50) is provided by means of the placement of the connector (54) to the connector housing (323).

Figure 6:
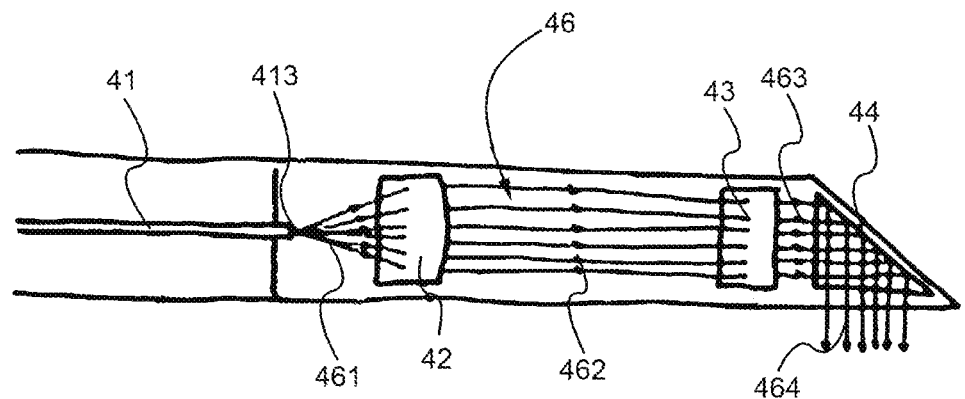
In FIG. 6, the schematic view of the laser rays of the laser processing mechanism is given.
Figure 7:
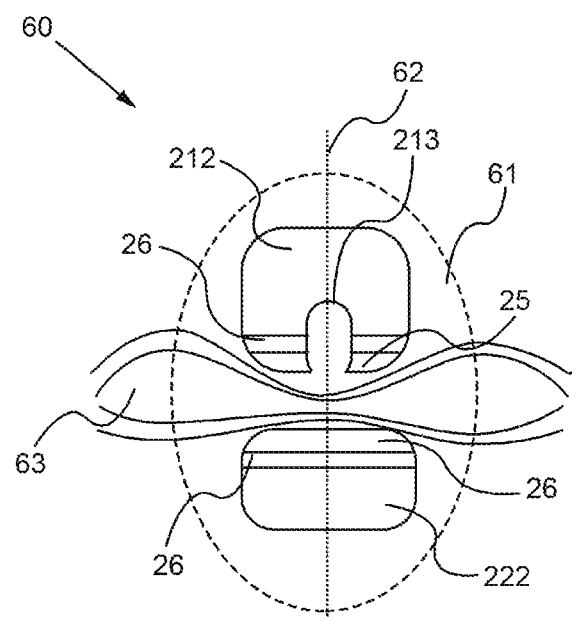
In FIG. 7, the schematic view of the operation region is given.

In FIGS. 6 and 7, the detailed views of laser processing mechanism (40) forming the inner structure of the laser module (30) are given. The laser processing mechanism (40) comprises an inner transmission line (41) connected to the transmission line (53) of the laser source (50), a regulatory lens (42), a focusing lens (43) and a prism (44) provided respectively after said inner transmission line (41) inside the outer body (31). At a position under said prism (44), an optical opening area (45) embodied at the tip part (311) is also provided in the laser processing mechanism (40). The inner transmission line (41) is fixed inside the outer body (31) by means of a primary fixation part (411) and a secondary fixation part (412). The end of the inner transmission line (41) defines a line opening (413). By means of the energy provided by the laser source (50), a light beam (46), which is carried and directed inside the outer body (31), exits through said line opening (413). When said light beam (46) exits the line opening (413), it forms the main light beam (461). Said main light beam (461) passes through said regulatory lens (42), and it is transformed into the linear light beam (462), and it is transmitted to said focusing lens (43). The linear light beam (462) exits the focusing lens (43) as focused light beam (463) and it is transmitted to said prism (44). The focused light beam (463), arriving at the prism (44), exits the prism (45) as a light beam (464) directed at a substantially orthogonal angle and it reaches said optical opening area (45).

The connection between the surgical equipment (20) and the laser module (30) is provided by means of placement of the external removable laser module (30) into said module housing (215). The outer body (31) is positioned at the lower body (21) in a manner extending inside the module housing (215). During this positioning, while the module connection pin (321) is placed to the module connection housing (216), the connection tabs (214) are placed to the tab opening (322) and they provide fixation of the connection part (32) on the lower body (21) and fixation of the outer body (31) in the lower body (21). As a result of this positioning, the trigger (217) and the safety lock (218) are provided on the triggering region (312). At the same time, the optical opening (213) provided at the upper jaw (212) and the optical opening area (45) are aligned.

In the direction of these details, the operation of the invention is as follows. The tissue (63), whose vessels are to be cut and sealed, is grabbed by means of a holder tip (24) of the surgical equipment (20) which defines a grabbing region (61). This grabbing is provided by means of proximation of the lower jaw (222) and the upper jaw (212) to each other by means of the handle (211) and the gripping handle (221). By means of this process, trigger (217) is pulled simultaneously, and as the trigger (217) is pulled, the laser source (50) becomes active. In order to provide activation of the system as the trigger (217) is pulled, the module connection pin (321) must be placed to the module connection housing (216) and it must complete the circuit.

By means of the energy transmitted from the laser tube (51), the laser generator (52) generates a laser light beam (46) and this laser light beam (46) is transmitted to the inner transmission line (41) by means of the transmission line (53) and the connector (54) and it is transmitted to the regulatory lens (42) as a main light beam (461). The light, which exits the regulatory lens (42) as linear light beam (462), enters into the focusing lens (43) and it exits as focused light beam (463) and it is transmitted to the prism (44). The directed light beam (464) transmitted through the optical opening area (45) by the prism (44) exits the optical opening (213) provided at the upper jaw (212). The directed light beam (464) shows effect in the grabbing region (61) in a laser axis (62) which is parallel to the transversal cross section of the vessel. The directed light beam (464), exiting the optical opening (213), realizes the cutting and sealing process as a result of the effect of the pressure formed between the lower jaw (222) and the upper jaw (212) such that said directed light beam (464) is effective only on the related vessels and surrounding tissue (63) existing in the operation region (60) included in the grabbing region (61) and such that it does not emit heat to the other areas. The prevention of heat emission to the areas which is outside the grabbing region (61) is provided by means of thermo-stable surface coating (26). Besides, thanks to the flexibility of the thermo-stable part (25), the effect for tightening the tissue (63) during holding of the tissue (63) is increased.

In said invention, the vessel walls are joined to each other by means of controlled laser energy beside the mechanical tightening, and both the sealing and cutting processes can be realized simultaneously. By means of the used triggering system, an increased usage safety is obtained. Moreover, by means of usage of disposable surgical equipment (20), different methods which cover all of the open and endoscopic surgical interventions, can be used.

The invention claimed is:

1. A vessel sealing and cutting system (10) comprising a surgical equipment (20) comprising a lower jaw (222) and an upper jaw (212) in a manner defining a holder tip (24) that grabs the vessels in tissues having vessels, and a lower body (21) embodied at the continuation of said upper jaw (212), and a laser source (50) connected to said surgical equipment (20), characterized by comprising a module housing (215) embodied in a manner extending inside said lower body (21) and said upper jaw (212), and a laser module (30) positioned in said module housing (215) which transmits a laser light to the grabbing region (61) from said holder tip (24) in a simultaneous manner with the closing of the jaws in a manner connected to said laser source (50) from one end thereof, said laser module (30) comprises an outer body (31) placed into the lower body (21) and a tip part (311) is embodied at the continuation of the outer body (31) placed into the upper jaw (212), wherein an optical opening (213) is embodied at the upper jaw (212) in a manner providing transmission of the light directed from the upper jaw (212) to the grabbing region (61) through the tin part (311), a laser processing mechanism (40) is provided in said outer body (31) in a manner providing direction of the light generated by the laser source (50), through the optical opening (213), said laser processing mechanism (40) comprises an inner transmission line (41) connected to the laser source (50), and a regulatory lens (42), a focusing lens (43) and a prism (44) positioned inside the outer body (31) respectively and which transmit a light, exiting said inner transmission line (20, 41), to the tip part (311).

2. The vessel sealing and cutting system (10) according to claim 1, wherein a triggering region (312), which is aligned with a trigger (217) provided on the surgical equipment (20) as the laser module (30) is placed to the lower body (21), is embodied on the outer body (31).

3. The vessel sealing and cutting system (10) according to claim 1, wherein a connection part (32) is provided at one end of the outer body (31), and a connector housing (323) is positioned at the end of said connection part (32) and whereto said laser source (50) is connected.

4. The vessel sealing and cutting system (10) according to claim 3, wherein a tab opening (322) is embodied at said connection part (32) and a module connection pin (321) is provided under the connection part (32).

5. The vessel sealing and cutting system (10) according to claim 2, wherein at least one connection tab (214) is provided at the lower body (21) in a manner corresponding to said tab opening (322).

6. The vessel sealing and cutting system (10) according to claim 4, wherein in order to provide completion of the circuit such that the system interacts with the laser source (50), a module connection housing (216), wherein said module connection pin (321) is placed, is embodied at the lower body (21).

7. The vessel sealing and cutting system (10) according to claim 1, wherein the laser processing mechanism (40) comprises an optical opening area (45) embodied at the tip part (311) which will provide direction of the light (311), exiting the prism (44), to the optical opening (213).

8. The vessel sealing and cutting system (10) according to claim 1, wherein the inner transmission line (41) comprises a primary fixation part (411) and a secondary fixation part (412) for providing fixation of the inner transmission line (41) and a line opening (413) embodied at the end of the inner transmission line (41).

9. The vessel sealing and cutting system (10) according to claim 8, wherein the light, transmitted from the line opening (413) of the transmission line (41) to the optical opening area (45), is a light beam (46).

10. The vessel sealing and cutting system (10) according to claim 9, wherein the light beam (46), which exits the line opening (45) and which is transmitted to the regulatory lens (42), is a main light beam (461).

11. The vessel sealing and cutting system (10) according to claim 8, wherein the light beam (46), which exits the regulatory lens (42) and which is transmitted to the focusing lens (43), is a linear light beam (462).

12. The vessel sealing and cutting system (10) according to claim 8, wherein the light beam (46), which exits the focusing lens (43) and which is transmitted to the prism (44), is a focused light beam (463).

13. The vessel sealing and cutting system (10) according to claim 8, wherein the light beam (46), directed from the prism (44) to the optical opening area (45), is a directed light beam (464).

14. The vessel sealing and cutting system (10) according to claim 1, wherein a thermostable part (25) is provided where said lower jaw (222) and said upper jaw (212) are covered in a manner increasing the tightening effect of the tissue.

* * * * *